United States Patent [19]

Veerapandian

[11] Patent Number: 5,349,051
[45] Date of Patent: Sep. 20, 1994

[54] MODIFIED INTERLUEKIN-1β

[75] Inventor: Balasubramanian Veerapandian, Rockville, Md.

[73] Assignee: University of Maryland, College Park, Md.

[21] Appl. No.: 13,663

[22] Filed: Feb. 4, 1993

Related U.S. Application Data

[63] Continuation of Ser. No. 649,568, Feb. 5, 1991, abandoned.

[51] Int. Cl.$^5$ ............................................. C07K 13/00
[52] U.S. Cl. .................................. 530/351; 930/141; 435/69.52; 424/85.2
[58] Field of Search ...................... 530/351; 930/141; 435/69.52; 424/85.2

[56] References Cited

U.S. PATENT DOCUMENTS

| | | | |
|---|---|---|---|
| 5,047,505 | 9/1991 | Huang | 435/172.3 |
| 5,116,943 | 5/1992 | Koths et al. | 530/351 |

FOREIGN PATENT DOCUMENTS

| | | |
|---|---|---|
| 0237967 | 9/1987 | European Pat. Off. |
| 2169600 | 6/1990 | Japan |
| 2223595 | 9/1990 | Japan |
| WO90/10068 | 9/1990 | PCT Int'l Appl. |
| 9206114 | 4/1992 | World Int. Prop. O. |

OTHER PUBLICATIONS

Chang et al, *Biochem.* 31, 1992, pp. 2874–74.
Young et al, *Lymphokine,* 9, 1990, p. 599.
Labrida-Tompkins et al., *PNAS* 88, 1991, pp. 11182–11186.
Creyhton et al, *Nature,* 339, 1987, pp. 14–15.
Subramanian, *Biotechnology* vol. 3 1985, p. 597.
Van Brunt, *Biotechnology* vol 7, 1989, pp. 324–325.
Fetrow et al, *Biotechnology* vol. 6, 1988, pp. 167–171.
King, *Biotechnology* vol. 4, 1986, pp. 297–303.
King, *C and EN News* Apr. 10, 1989, pp. 32–54.
Alker, *Annu Rev Biochem.* 1989, pp. 765–798 vol 58.
Leszcynski et al, *Nature* vol 234, 1986, pp. 849–855.
March et al *Nature* 315, 1985 p. 641.
Gehrke et al, *FBC* 265(11) 1990, pp. 5922–5925 (abstract only).
Wingfield et al, *Eur J Biochem* 179, 1989, pp. 565–571.
Kamogashira et al, *Biochem Biophy Res Comm* 150, 1988, pp. 1106–1114 (abstract only).
Ferreira et al, *Nature* 334, 1988, pp. 698–700.
Paloszynoki, *Biochem Biophys Res Comm* 147, 1987, pp. 204–211.
Pratta et al, *Agents Action* 34, 1991, pp. 60–62 (abstract only).
Yamayoshi et al, *Lymphokine Res,* 9, 1990, pp. 405–413 (abstract only).
Zucali et al, *Exp Hematol* 18, 1990, pp. 1078–1082 (abstract only).
Bradford J. Graves et al., "Structure of Interleukin 1 alpha at 2.7–A Resolution", Biochemistry, 1990, vol. 29, pp. 2679–2684.
B. Veerapandian et al., "Functional Implications of Interleukin-1 β Based on the Three–Dimensional Structure", Proteins: Structure, Function, and Genetics, Jan. 1992, vol. 12, No. 1, pp. 10–23.
H. Robson MacDonald et al., "Point mutations of human interleukin-1 with decreased receptor binding affinity", Febs Letters, Dec. 1986, vol. 209, No. 2, pp. 295–298.

*Primary Examiner*—Garnette D. Draper
*Attorney, Agent, or Firm*—Oblon, Spivak, McClelland, Maier & Neustadt

[57] ABSTRACT

The present invention relates to modified forms of IL-1β with altered IL-1β activity. The modified IL-1β is the result of mutations which affect amino acids in the beta barrel portion of the IL-1β structural formula. The invention also relates to expression systems that will produce the modified IL-1β polypeptides, and methods of treating susceptible diseases with the modified IL-1β pol

MODIFIED INTERLUEKIN-1β

This application is a continuation of application Ser. No. 07/649,568, filed Feb. 5, 1991.

BACKGROUND OF THE INVENTION

The term interleukin-1 (IL-1) refers to two different polypeptides (IL-1α and IL-1β). These two polypeptides possess a wide variety of both immunologic and nonimmunologic activities. IL-1α and IL-1β are distinct gene products. However, these two polypeptides recognize the same receptor and exhibit the same biological properties. IL-1 is produced in response to a variety of conditions including inflammatory agents, toxins, infection and clotting components. The primary amino acid sequence of human IL-1α and IL-1β have been reported (Auron et al., *Proc. Natl. Acad. Sci. USA*, 81, 7907 (1984); and March et al., *Nature* 315, 641 (1985), respectively). Furthermore, the entire human gene for each form of IL-1 has been cloned and sequenced (Clark et al., *Nucleic Acids Res.* 14, 7897 (1986); Furutani et al. *Nucleic Acids Res.* 14, 3167 (1986)).

IL-1 is a small protein of molecular weight about 17.5 kilodaltons, which induces sleep and systemic acute-phase responses including fever, increased hepatic acute-phase protein synthesis, neutrophilia, hypozincemia, hypoferremia and increased levels of hormones when injected into experimental animals. Although IL-1α and IL-1β have been shown to have distinct primary amino acid sequences (only about 26% amino acid sequence homology), these two polypeptides have been shown to be structurally related by molecular modeling, receptor recognition and crystallographic analysis.

The three dimensional structure of IL-1β has 12 β strands which form a complex of hydrogen bonds as shown by analysis of the tertiary structure of crystallized human IL-1β and computerized molecular modeling. The basic structure is similar to a tetrahedron with an interior filled by hydrophobic side chains. Therefore, the interior of IL-1β is strongly hydrophobic with no charged amino acids.

IL-1β is the more prominent of the two known gene products for IL-1, as evidenced by the greater amount of IL-1β found in culture supernatants and various human body fluids. Furthermore, the amount of IL-1β mRNA found in activated cells is usually about 10 to 50 times greater than the amount of IL-1α found in these same cells. IL-1β is more readily secreted from activated cells, whereas IL-1α remains cell-associated.

IL-1β was originally cloned from human blood monocytes, and has subsequently been cloned in cows, rabbits, rats and mice. IL-1α was originally cloned from the mouse macrophage cell line P388D, and has subsequently been cloned in humans, rabbits and rats.

Several peptides which exhibit some of the same biological properties as IL-1 have been either synthesized (Antoni et al., *J. Immunol.* 137, 3201 (1986)) or produced by recombinants DNA methods (Rosenwasser et al., *Proc. Natl. Acad. Sci. USA* 83, 5243 (1986)). However, the specific activities of these peptides are low, and the peptides do no block the receptor binding of mature IL-1. Conventional theories suggest that both the N-terminal and C-terminal amino acids of IL-1 are involved in its receptor binding (Dinarello, *Advances in Immunology* 44, 153 (1989)).

The histidine residue at position 147 has been substituted by site-specific mutation with a resulting loss of biological activity and receptor binding (MacDonald et al., *FEBS Lett.* 209, 295 (1986)). However, this histidine residue is located on the surface of the IL-1β molecule.

Other mutations of IL-1β N-terminal amino acids have also resulted in altered biological activity and receptor binding (Horuk et al., *J. Biol. Chem.* 262, 16275 (1987)). These mutations also suggest that the N-terminal amino acids of IL-1β play an important role by direct interaction with receptor-binding domains.

However, the IL-1β mutants produced to date have not been found to be significantly effective in minimizing, or more importantly, antagonizing the biological activities of IL-1. Such an antagonist of IL-1 would be particularly useful in the treatment of patients with bacterial infection, injury or chronic inflammatory disease.

SUMMARY OF THE INVENTION

The present invention overcomes the inherent limitations of previously proposed mutants of IL-1 by providing modified structures of IL-1β which result in either IL-1 agonist or antagonist activity.

In accordance with the invention, the modified IL-1β with altered IL-1 activity comprises the IL-1 polypeptide with at least one mutation to the beta barrel portion of the IL-1β structural formula. The invention also relates to expression systems which will produce the modified IL-1β polypeptides, as well as methods of treating diseases by administering an effective amount of the modified IL-1β polypeptides.

BRIEF DESCRIPTION OF THE DRAWINGS

The various aspects, advantages and novel features of the present invention will be more clearly understood from the following detailed description when read in conjunction with the appended drawings in which.

DETAILED DESCRIPTION OF THE INVENTION

Figure 2:
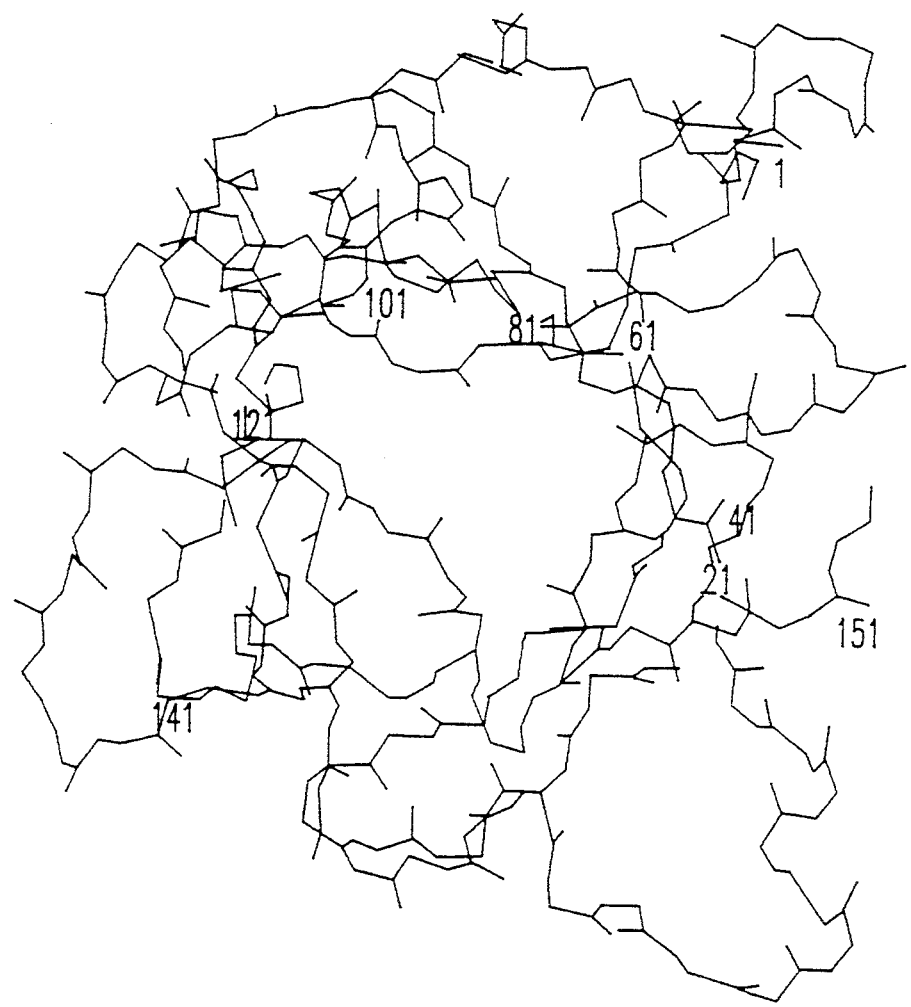
FIG. 2 is a computerized representation of the molecular structural formula of IL-1β.

In order to provide a clear and consistent understanding of the specification and the claims, the following definitions are provided:

Beta barrel: A portion of the molecular structural formula of IL-1β. The beta barrel is composed of twelve antiparallel β strands exhibiting a pseudo three-fold symmetry. The beta barrel has a concentration of polar residues on both of its ends. The beta barrel of interleukin-1β is depicted in the computerized models shown in FIG. 2.

Cell Culture: A proliferating mass of cells which may be in an undifferentiated or differentiated state. As used herein "cell line", and "cell culture" are used interchangeably and all such designations include progeny. Thus "transformants" or "transformed cells" includes the primary subject cell and cultures derived therefrom without regard for the number of transfers. It is also understood that all progeny may not be precisely identical to DNA content, due to deliberate or inadvertent mutations. Mutant progeny which have the same functionality as screened for in the originally transformed cell, are included. Where distinct designations are intended, it will be clear from the context.

Coding Sequence: A deoxyribonucleotide sequence which when transcribed and translated results in the formation of a cellular protein, or a ribonucleotide sequence which when translated results in the formation of a cellular protein.

Control Sequences: Refers to DNA sequence necessary for the expression of an operably linked coding sequence in a particular host organism. The control sequences which are suitable for procaryotes, for example, include a promoter, optionally an operator sequence, a ribosome binding site, and possibly, other as yet poorly understood, sequences. Eucaryotic cells are known to utilize promoters, polyadenylation signals, and enhancers.

Expression System: Refers to DNA sequences containing a desired coding sequence and control sequences in operable linkage, so that hosts transformed with these sequences are capable of producing the encoded proteins. In order to effect transformation, the expression system may be included on a vector; however, the relevant DNA may then also be integrated into the host chromosome.

Gene: A discrete nucleic acid region which is responsible for a discrete cellular product.

Operably Linked: Refers to juxtaposition such that the normal function of the components can be performed. Thus, a coding sequence "operably linked" to control sequences refers to a configuration wherein the coding sequence can be expressed under the control of these sequences.

Promoter: The 5'-flanking, non-coding sequence adjacent a coding sequence which is involved in the initiation of transcription of the coding sequence.

With the above definitions in mind, the present invention broadly relates to modified or mutated forms of IL-1$\beta$. Some of the modifications result in peptide compositions which cause biological effects that mimic the biological effects of interleukin-1 (i.e. IL-1 agonists). Other modifications result in compositions which cause biological effects which nullify the biological effects of interleukin-1 (i.e. IL-1 antagonists). However, all of the resulting peptide compositions differ from IL-1$\beta$ by a modification or mutation to at least one amino acid in the beta barrel portion of the IL-1$\beta$ structure.

The effect of the modification or mutation to an amino acid in the beta barrel of the IL-1$\beta$ structure may be either direct or indirect. Direct effects are modifications or mutations of the target amino acid in the beta barrel. Indirect effects to an amino acid in the beta barrel are modifications or mutations of at least one amino acid other than the target amino acid in the beta barrel.

A modification which results in an indirect effect to an amino acid in the beta barrel is a modification to an amino acid proximate to the target amino acid. However, the proximate amine acid that is modified to produce an indirect effect may be an amino acid which is not in the beta barrel, or an amino acid which is also in the beta barrel.

A modification which results in an indirect effect to a target amino acid in the beta barrel may be a modification which neutralizes the charge of the target amino acid, neutralizes the acidity or basicity of the target amino acid, effects the hydrophilicity or hydrophobicity of the target amino acid, or alters the steric position of the target amino acid. These same effects are also the result of direct modification of the target amino acid itself.

The direct modifications of the IL-1$\beta$ structure which are of particular interest are:

1) A mutation of Glu25 to Ala which inhibits the biological activity of IL-1$\beta$, but still permits binding of the modified polypeptide to the IL-1 receptor.
2) The mutation of Glu25 to Ala and the mutation of Lys103 to Ala which also inhibits the biological activity of IL-1$\beta$.
3) The mutation of Glu25 to Ala, Lys103 to Ala, and the mutation of Cys8, Met44, and/or Met148 to either Ala or Gly to inhibit the biological activity of IL-1$\beta$.

The indirect modification of the IL-1$\beta$ structure which is of particular interest is the mutation of Ser21 to Arg which results in the neutralization of the negative charge of Glu25, thereby inhibiting the biological activity of IL-1$\beta$.

The modified interleukins of the present invention (including those listed above) were proposed following close examination of the three dimensional structure of IL-1$\beta$, and review and evaluation of previous attempts to modify the IL-1$\beta$ structure to obtain compounds with IL-1$\beta$ antagonist activity. This review and evaluation led to the conclusion that IL-1$\beta$ binds to its receptor in a manner contrary to conventional receptor binding theory.

Figure 1A:
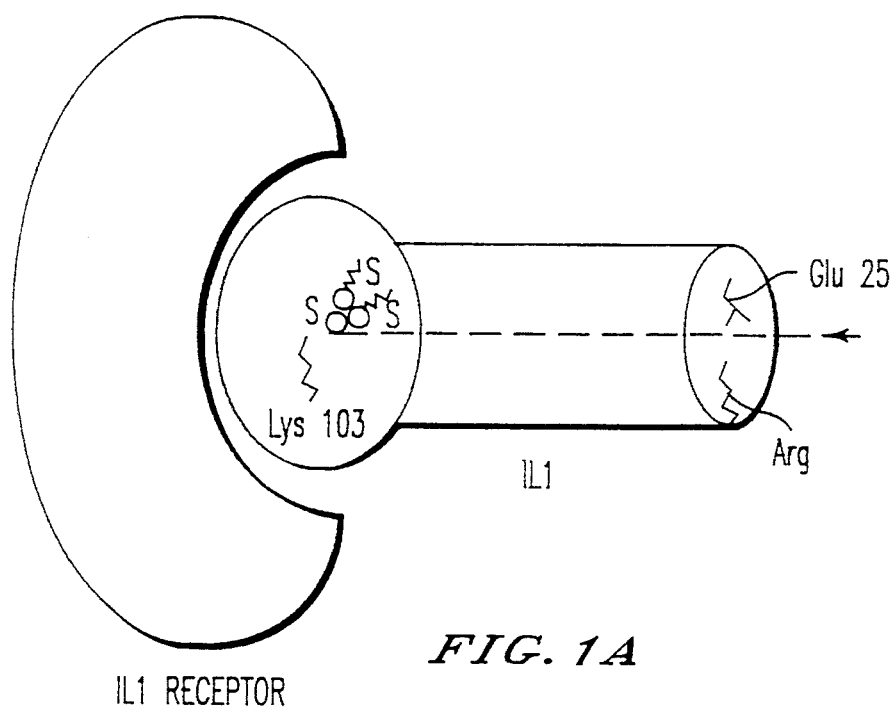
FIGS. 1A and 1B are schematic depictions of the IL-1β molecule and its receptor.
Figure 1B:
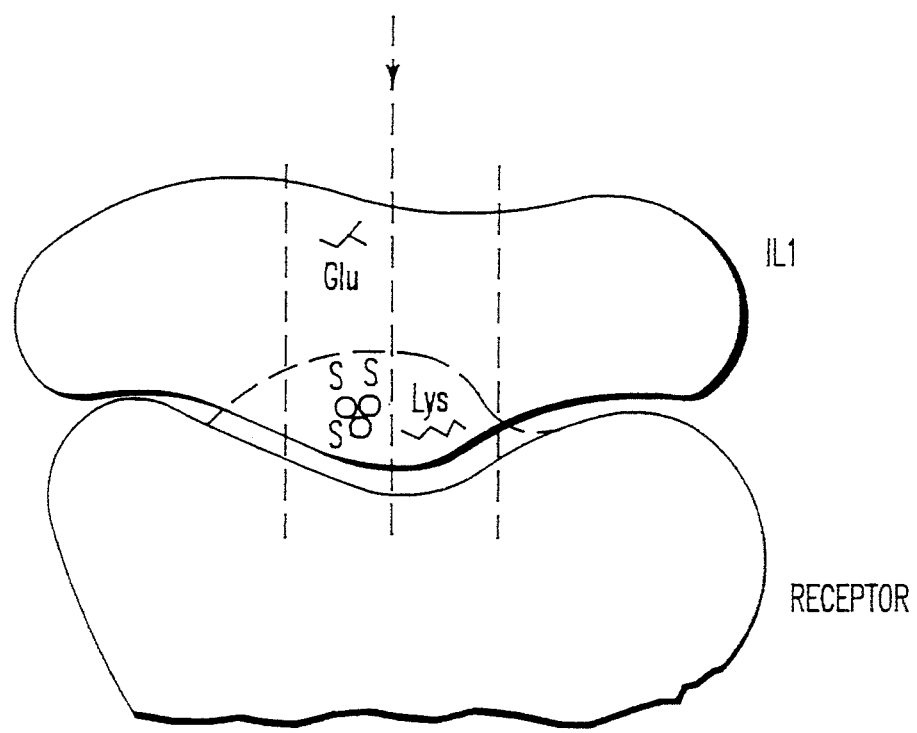

Conventional receptor binding theory suggests that the IL-1$\beta$ molecule binds to its receptor at a single point or along a very narrow section of the molecule. However, the present inventor found that the IL-1$\beta$ molecule binds to its receptor in a broad manner, or surface to surface, as depicted in FIGS. 1A and 1B. This unconventional surface to surface binding of IL-1$\beta$ to its receptor is supported by previous mutations of the IL-1$\beta$ molecule, and by the similarities of the molecular structures of IL-1$\beta$, IL-1$\alpha$ and known IL-1 antagonists.

Previous mutations of the IL-1$\beta$ molecule have resulted in inefficient binding of the mutant to the IL-1 receptor (Priestle et al., *EMBO J.* 7, 339 (1988)). However, these previous mutations have been distant from one another, rather than in close proximity. Yet even distant mutations result in inefficient binding of the different mutants to the receptor. Therefore, more than a single point or narrow band of the IL-1$\beta$ molecule is binding to the receptor. Instead, a broad surface is binding to a broad surface of the receptor as depicted in FIGS. 1A and 1B. Hence, even mutations at sites distant from one another on the binding surface of the IL-1$\beta$ molecule will cause similar results of inefficient binding of the IL-1$\beta$ molecule to its receptor.

Furthermore, the molecular structures of IL-1$\beta$, IL-1$\alpha$ and known IL-1 antagonists all have basic similarities. These basic similarities all relate to the beta barrel portion of the molecules. All of these molecules have the unique structural folding which produces the beta barrel structural characteristic. Furthermore, the key amino acid residues of IL-1$\beta$ (Glu25, Lys103 and part of the sulfur cluster) are also present at the same locations on the beta barrel of the IL-1$\alpha$ structure, although not at the same locations in the amino acid sequence. However, the known IL-1 antagonists lack these three key amino acid residues.

Using this knowledge, the inventor examined the molecular structure of IL-1$\beta$ as described in Examples 1 and 2, below. The inventor then found that the surface at the end of the IL-1β beta barrel was the type of surface that would be appropriate for the necessary surface to surface binding with the receptor.

Although barrel structures in other molecules are commonly utilized to transport ions, the beta barrel of IL-1β is too narrow to perform such a task. Also, the inventor noted that there are oppositely charged focal amino acids at the opposite ends of the beta barrel. While a positively charged lysine (Lys103) is located in the beta barrel surface that binds to the receptor, a negatively charged aspartic acid (Glu25) is located at the surface of the beta barrel which is furthest from the receptor (see FIGS. 1A and 1B). Also noted was a sulfur cluster of -Cys8-Met44-Met148- which is located in the beta barrel, on the axis between the oppositely charged Lys103 and Glu25.

It is mutations at these three foci of the beta barrel which result in the modified forms of IL-1β of the present invention. The mutations may be to the target amino itself or to proximate amino acids in order to affect the target amino acid. The mutations that affect Lys103 or Glu25 at opposite ends of the beta barrel are mutations which nullify the charge of Lys103 and/or Glu25.

The mutations which affect Glu25 generally result in modified forms of IL-1β that act to antagonize the effect of IL-1β, and strongly bind to the IL-1 receptor. These modified forms of IL-1β maintain the strong receptor binding characteristics of IL-1β because the mutation affects a target amino acid (Glu25) which is not on the surface of the molecule which binds to the receptor. The antagonist activity of such modified forms of IL-1β are the result of partial or total neutralization of the negative charge of Glu25.

The neutralization of the negative charge of Glu25 may be accomplished by either direct mutation of the target glutamic acid (Glu25) or mutation of a proximate amino acid to effect the negatively charged Glu25. Direct mutations of Glu25 to neutralize its negative charge include mutations to alanine, glycine, valine, leucine, isoleucine, phenylalanine, (i.e. non polar groups). Of these direct mutations, the preferred mutation is the replacement of Glu25 with alanine (i.e. Ala25). This mutation results in inhibition of the IL-1β effects of the protein without affecting the protein's binding to the IL-1 receptor. Of the mutations of other amino acids to indirectly affect the target amino acid (Glu25), the preferred mutation is the replacement of the serine at position 21 (Ser21) with an arginine (Arg21). This mutation also causes a neutralization of the negative charge of Glu25 to invalidate the IL-1β affects of the protein without affecting the protein's binding to the IL-1 receptor.

However, direct mutations of Glu25 are one of the most preferred embodiments of the invention relating to modified IL-1β with IL-1β antagonist properties, because these modifications are the most similar to known, natural IL-1β antagonists. The known naturally occurring IL-1β antagonists have a Gln24, neutralized by Arg21.

In addition to the mutations to affect Glu25, mutations to affect Lys103 are also effective to produce modified IL-1β with IL-1β antagonist properties. However, direct mutations of Lys103 also have an affect on the binding of the molecule to the IL-1 receptor, because Lys103 is located on the surface of the beta barrel that binds to the receptor. The most effective mutation of Lys103 to produce a modified IL-1β with antagonist properties is the replacement of Lys103 with alanine (i.e. Ala103). However, this mutation may produce a more potent IL-1β antagonist when coupled with the direct mutation of Glu25 to Ala25.

Furthermore, complete inhibition of IL-1β effects is achieved with the two above mutations (Glu25Ala and Lys103Ala) and a mutation of the sulfur cluster (Cys8, Met44, Met148) to alanine and/or glycine. This sulfur cluster is necessary for the strong effects of IL-1β. Therefore, mutation of this sulfur cluster to alanine and/or glycine completely invalidates IL-1β agonist activity. Furthermore, it is expected that the degree of inhibition of the IL-1β effects of the modified IL-1β molecules may be modulated by mutating only one or two of the amino acids of the sulfur cluster rather than all three amino acids.

Other compositions also have molecules with a barrel structure which is too narrow to transport ions, and therefore similar mutations to these molecules are expected to have similar results as the mutations to the IL-1β molecule. Among other compositions, IL-1α, fibroblast growth factor and tumor necrosis factor are such compositions with molecules exhibiting a barrel structure similar to that of IL-1β.

All of the above mutations are accomplished by the techniques of site-directed mutagenesis of cloned DNA which are conventional in the art. Such techniques are fully explained in *Molecular Cloning, A Laboratory Manual*, Second Edition, Sambrook et al., Cold Spring Harbor Laboratory Press 1989, incorporated herein by reference. However, these mutations may also be accomplished by cleaving the IL-1β gene near the target mutation site, and applying standard polymerase chain reaction (PCR) techniques with mismatched primers. The PCR products (with the desired mutations are then annealed to the unmutated segments of the cleaved IL-1β gene.

Having determined that Glu25, Lys103 and the sulfur cluster -Cys8-Met44-Met148 are the important functional areas of the IL-1β molecule (as explained above), new, smaller agonist and antagonist peptides can be synthesized by utilizing these target areas. One basic form of these synthetic agonist peptides has just the three functional areas of the IL-1β molecule. Thus, this synthetic agonist peptide has the amino acid sequence designated SEQ ID NO. 1, and serves as a substitute for IL-1β.

Similarly, any synthetic peptide which contains a lysine (Lys) on one side of the sulfur cluster (-Cys-Met-Met-) and an glutamic acid (Glu) on the other side of the sulfur cluster, even with other amino acid residues inserted between these functional groups, may act as an agonist, and mimic the effects of IL-1β. These synthetic peptide agonists are small dipole peptides with a sulfur cluster between the dipole, and are produced using standard peptide synthesis techniques. However, once these IL-1β peptide agonists have been synthesized, conventional degenerative primer techniques may be utilizing to produce the synthetic IL-1β agonists with the polymerase chain reaction (PCR).

Furthermore, these smaller synthetic peptide agonists can be mutated to produce small synthetic peptide antagonists. The mutations are directed at the same three target locations, namely the aspartic acid which corresponds to Glu25 of IL-1β, the lysine which corresponds to Lys103, and the sulfur cluster which corresponds to -Cys8-Met44-Met148. However, due to the smaller size of the synthetic peptide, the mutations are preferably direct mutations of the target amino acids rather than mutations of proximate amino acids in order to affect the target amino acid.

Moreover, the sulfur cluster (-Cys-Met-Met-) can be used by itself or in a larger peptide as an enhancer of IL-1β activity or as IL-1β agonists. The sulfur cluster will enhance the effects of IL-1β. Therefore, a smaller molecule which contains this sulfur cluster can act as an enhancer of IL-1β activity when administered in conjunction with IL-1β or a synthetic IL-1β agonist.

Any of the modified IL-1β compounds (or small peptide IL-1β agonists or antagonists, or the sulfur cluster enhancers) can be produced by appropriate expression systems using conventional recombinant nucleotide techniques. The control sequences, expression vectors, and transformation methods are dependent on the type of host cell used to express the gene. Generally, procaryotic, yeast, or mammalian cells are presently useful as hosts. Procaryotic hosts are in general the most efficient and convenient for the production of recombinant proteins. However, eucaryotic cells, and, in particular, mammalian cells are sometimes used for their processing capacity.

The procaryotes most frequently used as hosts are represented by various strains of *E. coli*. However, other microbial strains may also be used, such as bacilli, for example *Bacillus subtilis*, various species of Pseudomonas, or other bacterial strains. In such procaryotic systems, plasmid or bacteriophage vectors which contain replication sites and control sequences derived from a species compatible with the host are used. A wide variety of vectors for many procaryotes are known (Sambrook et al., (1989), *Molecular Cloning: A Laboratory Manual*, 2nd Ed., Cold Spring Harbor Laboratory, Cold Spring Harbor, N.Y.). Commonly used procaryotic control sequences which are defined herein to include promoters for transcription initiation, optionally with an operator, along with ribosome binding site sequences, include such commonly used promoters as the beta-lactamase (penicillinase) and lactose (lac) promoter systems, the trytophan (trp) promoter system and the lambda derived PL promoter and N-gene ribosome binding site, which has been made useful as a portable control cassette (U.S. Pat. No. 4,711,845). However, any available promoter system compatible with procaryotes can be used (Sambrook et al., supra).

In addition to bacteria, eucaryotic microbes, such yeast, may also be used as hosts. Laboratory strains of Saccharomyces ceresisiae, Baker's yeast, are most used, although a number of other strains are commonly available. Vectors employing the 2 micron origin of replication and, other plasmid vectors suitable for yeast expression are known (Sambrook et al., supra). Control sequences for yeast vectors include promoters for the synthesis of glycolytic enzymes. Additional promoters known in the art include the promoter for 3-phosphoglycerate kinase, and those for other glycolytic enzymes, such as glyceraldehyde-3-phosphase dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglycose isomerase, and glucokinase. Other promoters, which have the additional advantage of transcription controlled by growth conditions, are the promoter regions for alcohol dehydrogenase 2, isocytochrome C, acid phosphates, degradative enzymes associated with nitrogen metabolism, and enzymes responsible for maltose and galactose utilization. (See Sambrook et al., supra).

It is also believed terminator sequences are desirable at the 3' end of coding sequences. Such terminators are found in the 3' untranslated region following the coding sequences in yeast-derived genes. Many of the vectors illustrated contain control sequences derived from the enolase gene containing plasmid peno46 or the LEU2 gene obtained from Yep13, however, any vector containing a yeast compatible promoter, origin or replication and other control sequences is suitable (Sambrook et al., supra).

It is also possible to express genes encoding polypeptides in eucaryotic host cell cultures derived from multicellular organisms (*Meth. Enzymol.*, Vol 58, Academic Press, Orlando (1979)). Useful host cell lines include murine myelomas N51, Vero and HeLa cells, and Chinese hamster ovary (CHO) cells. Expression vectors for such cells ordinarily include promoters and control sequences compatible with mammalian cells such as, for example, the commonly used early and later promoters from Simian Virus 40(SV 40), or other viral promoters such as those derived from polyoma, adenovirus 2, bovine papilloma virus, or avian sarcoma viruses, or immunoglobulin promoters and heat shock promoters (Sambrook et al., supra). General aspects of mammalian cell host system transformations have been described by Axel (U.S. Pat. No. 4,399,216).

It now also appears that "enhancer" regions are important in optimizing expression; these are, generally, sequences found upstream of the promoter region. Origins of replication may be obtained, if needed, from viral sources. However, integration into the chromosome is a common mechanism for DNA replication in eucaryotes. Plant cells are also now available as hosts, and control sequences compatible with plant cells such as the nopaline synthase promoter and polyadenylation signal sequences are available (*Meth. Enzymol.*, Vol 118, Academic Press, Orlando (1979)).

Depending on the host cell used, transformation is done using standard techniques appropriate to such cells. Such techniques include, but are not limited to, calcium treatment emplying calcium chloride for procaryotes or other cells which contain substantial cell wall barriers; infection with *Agrobacterium tumefaciens* for certain plant cells; calcium phosphate precipitation method for mammalian cells without cell walls; and, microprojectile bombardment for many cells including plant cells.

The compounds of the present invention are purified using conventional techniques as described in Kikumoto et al., *Biochem. Biophys. Res. Comm.* 147, 315 (1987). Furthermore, the biological activity of these compounds is evaluated by the standard murine (C3H/HeJ) thymocyte proliferation assay as described in Lachman et al., *Methods Enzymol.* 116, 467 (1985). Other useful tests for the biological activity of these compounds are the fibroblast prostaglandin $E_2$ production assay and the EL4/9 interleukin-2 production assay. The binding of the compounds of the invention to the IL-1 receptor is assayed by iodinating the compounds with Bolton Hunter reagent and binding the iodinated compounds to EL4/9 cells according to the methods of Dower et al., *Nature* 324, 266 (1986). In vitro tumor inhibitory activity of the IL-1β agonists is measured by the methods described in Nakamura et al., *Jap. J. Cancer Res. (Gann)* 77, 767 (1986). Briefly, C57BL/6 mice are transplanted with B16 melanoma cells intra-dermally on day 0, the compounds of the present invention in pharmaceutical composition are injected once daily on day 8 through 14, and inhibition rates are calculated on day 15.

The compounds of the present invention (the IL-1β agonists, the IL-1β antagonists, and the IL-1β agonist enhancers) may be either used in a pharmaceutical composition in their respective peptide forms, or may be attached to an appropriate peptide carrier to be used in pharmaceutical compositions. When used as the active ingredient in a pharmaceutical composition, the compounds of the present invention are admixed with an appropriate pharmaceutical carrier according to conventional pharmaceutical compounding techniques. The carrier may take a wide variety of forms depending on the form of preparation desired for administration, e.g., intravenous, oral or parenteral. The composition may also be administered by means of an aerosol. Although oral dosage forms are not preferred because the active ingredients are peptides which are degraded by enzymes in the gastrointestinal tract, conventional techniques for protecting the peptide from enzymatic digestion may be used. Such conventional techniques include enteric coating of tablets with agents such as mixtures of fats and fatty acids, shellac and shellac derivatives, and cellulose-acetate phthalates. The use of cellulose acetate phthalates is most common and preferred.

However, in preparing the compositions in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques.

Parental preparations of the active compounds of the present invention are preferred. For parenteral preparations, the carrier will usually comprise sterile water, though other ingredients, for example, to aid solubility or for preservative purposes, may be included; injectable suspensions may also be prepared, in which case appropriate liquid carriers, suspending agents and the like may be employed. The pharmaceutical compositions will generally contain a dosage per unit, e.g., tablet, capsule, powder, injection, teaspoonful and the like, from about 0.01 to about 50 mg/kg, and preferably from about 0.1 to about 10 mg/kg of the active ingredient.

The following examples describe the invention in greater particularity and are intended to be a way of illustrating but not limiting the invention.

EXAMPLE 1

Crystallization of IL-1β and Data Collection

Purified recombinant human IL-1β was supplied by Otsuka Pharmaceuticals, Japan. Crystals were grown by vapor diffusion using the hanging drop technique as described in Gilliland et al., (citation) (1987). These crystals are tetragonal with a=b=55.14(2) Å and c=76.66(4) Å and belong to the enantiomorphic pair of space group P4$_1$ or P4$_3$.

Diffraction X-ray intensity data were collected by using a Siemen's multiwire area detector. The X-ray source was a Rigaku ra200 rotating anode operating at 3.2 kW, equipped with a graphite monochromator. The chamber was set at 2θ=20°, where 2θ defines the angle between the normal to the center of the detector face and the undiffracted X-ray beam direction. Chamber to crystal distance was kept as 10 cm and a data set was collected to a resolution of 2.0 Å with a total of 25,706 observations, scaled to give an R$_{merge}$ of 0.05, where $$R_{merge} = \frac{\Sigma \;\mid\mid I_i - <I> \mid}{\mid I_i \mid}$$

Of the available 14,207 unique reflections, 11,013 having I>2σ(I) were used for the rest of the analysis and refinement. Reduction of these data to integrated intensities was carried out using the XENGEN software package (Howard et al., J. Appl. Crystallogr 20: 383–387 (1987).

Heavy Atom Derivatives and Use of Recombinant Technology

Of the 16 potential derivative data sets collected, only three were used in the structure solution. All the derivative data sets extended to a resolution of 3 Å. Difference Patterson maps of mercurial and few other derivatives showed a single major site, later to be identified with Cys8.

Interpretation of the single isomorphous map by using this site was difficult and confusing, even though some of the molecule's secondary structural features could be identified. Since IL-1β contains two cysteines, site directed mutagenesis was used to change one of the cysteines to alanine, in order to obtain a new derivative. Recombinant protein was prepared by mutating Cys8 to Ala8 without altering Cys71 and used to make heavy atom derivatives. Mutant derivative crystals were found to be isomorphous with those of wild type protein. Difference Patterson map of this brought out another heavy atom site, later confirmed to be closer to Cys71.

Scaling, merging and MIR steps were carried out using PROTEIN (Steigemann, "Protein: A program system for the crystal structure analysis of proteins" (Version 85), Ph.D. Thesis, Technical University, Munich, 1974) package. The x and y coordinates of the sites were determined from the Harker section w=½. Since the space group is an enantiomer of P4$_3$ or P4$_1$, wherein the origin is not defined, the z coordinate of the first site was given an arbitrary value of 0.1. The centric data alone were used in order to refine the spatial coordinates, occupancy, atomic temperature, factor, overall scale factor and relative temperature factor of these sites.

Differences Fourier and cross difference Fourier maps were computed to confirm these major sites and few other minor sites were also identified. Using these sites, native MIR phases were calculated to a resolution of 3.0 Å and computed electron density map showed defined chain directions. Computed minimap defined the boundary of the molecule and showed large amount of solvent space in the crystal lattice.

B. C. Wang's automated package (Wang, B. C., Methods Enzymol 115: 90–112 1985) for solvent flattening was employed to improve the quality of the MIR map and solvent filtering was done at a resolution of 3.0 Å.

This procedure improved the phasing, evident from the increase in the average figure of merit from 71% of MIR to 83%. The obtained Fourier map showed clear solvent-protein boundaries along with well defined electron density for extended β-strands.

FRODO (Jones & Thirup *Embo J.*, 819–822, 1986), which uses a protein data base of best refined protein structures, was used in order to interpret the electron density map. The skeletons of the map were obtained as 'bones' by connecting a set of points through the centroids of the continuous stretch of density. FRODO allows the obtained skeletons to be identified as probable main chain, possible main chain and side chain. Initially the chain was modelled as poly serine and later modified to the appropriate residues. Whenever the connectivity showed a loop or a turn, database search within FRODO was used to place the fragments in the background, a helping aid in building the difficult parts of the model. The twist observed in the β-strands ambiguously fixed the spacegroup of this system as $P4_3$ and not $P4_1$, confirming the model suggested by Priestle et al., *Proc. Natl. Acad. Sci, USA* 86:9967–9671, 1988.

Molecular Dynamics and Conventional Refinement

This 3.0 Å model was refined initially with X-PLOR (Brunger, *Crystallographic Computing 4: Techniques and New Technologies*, Isaacs, N. W. & Taylor, M. R., eds. pp. 126–140, Clarendon Press, Oxford, 1988), which employs molecular dynamics coupled with energy minimization techniques, operating on an Alliant FX 80 computer. Two different strategies were adopted for this simulated annealing (SA). As a first choice the undefined two loops were removed and the rest of the molecule was treated as three separate fragments. Simultaneously, as a second choice, these loops were built by using the available built-in database of FRODO (even though a few residues did not have reliable density), and the whole molecule was subjected to the SA procedure.

The initial R-factor before starting the simulated annealing was 47%. Conditions set were (1) the number of cycles of energy minimization was 240 with $\Delta f = 0.05$ Å ($\Delta f$ indicates how far any atom can move before the first derivative of the energy term due to diffraction data is updated), (2) heating stage of molecular dynamics, 0.5 ps, T=4000° K., timestep=1 fs, velocity scaling every 25 fs and $\Delta f$ of 0.2 Å, (3) cooling stage of molecular dynamics, 0.25 ps, T=300° K., timestep=1 fs, velocity scaling every 25 fs and $\Delta f$ of 0.2 Å, and (4) with 150 cycles of energy minimization and $\Delta f = 0.05$ Å.

The first cycle revealed a weak but continuous density in the above said surface loop regions, for both the options and the R factor dropped from 47% to 32%. The loops were built in and a second cycle of SA was done with 2.5 Å data. For the last cycle, the T was kept as 1000° K. Computed $4|F_o| - 3|F_o|$ and $|F_o| - |F_c|$ maps revealed the missing residues in the loops. At the end of the SA refinement the R factor was 25%.

The model was then subjected to restrained Least Squares refinement program RESTRAIN (Moss and Morffew, *Comput. Chem.* 6:1–3 1982; Haneef et al., *Acta Crystallogr.* A41:426–433, 1985), running on the Allient FX 80 computer. The parameters refined include the Cartesian coordinates and a mean square displacement or isotropic thermal parameter ($U_{iso}$) for each non-hydrogen atom. All non-hydrogen atoms were refined with a fixed occupancy factor of unity. Minimum target interatomic restrain distances were used to remove unfavorable van der Waals contacts. No restraints between the $U_{iso}$ values of neighboring atoms were applied. Planarity restraints were applied to the rings of histidine, phenylalanine, tryptophan and tyrosine residues, side chain carbonyls and amides, and to a lesser degree to peptide planes of the main chain. The chiral restraints were applied as distance restraints along the edges of the chiral tetrahedra. Progress was monitored by a calculation of the crystallographic R-factor $$R = \frac{\Sigma \, || \, F_o| - G \, | \, F_e \, ||}{\Sigma \, | \, F_o \, |},$$

where G is scale factor. Structure factor amplitudes were weighted by the modified function *Cruickshank, Computing Methods in Crystallography*, Rollet, J. S., ed., pp. 114–115, Permagon Press, Oxford, 1965.

The weights of the distance restraints at the end of the refinement were adjusted such that the r.m.s. deviations of the target values from the ideal values were as small as possible. Atomic coordinates, an overall scale and an overall temperature factor were refined for the first few cycles and only later were individual isotropic temperature factors allowed to change.

At this stage, unidentified peaks in the difference Fourier maps were assigned to water molecules. A total of 55 such water molecules were identified and included in subsequent refinement. The least squares refinement was performed progressively by increasing the resolution of the data from 2.5 Å to 2.0 Å. Throughout the refinement the weights for the geometric restraint classes were varied in order to obtain a model with reasonable geometry and expected r.m.s. deviation. Additional 60 water molecules were identified during further cycles of refinement and remodeling to electron density maps.

EXAMPLE 2

Analysis of the Structure of IL-1β

The final R-factor for reflections between 20 and 2.0 Å resolution is 0.19. Atomic coordinates have been deposited with the Protein Data Bank (Bernstein et al., *J. Mol. Biol.* 112:535–542, 1977). Finzell et al., *J. Mol. Biol.* 209:779–791, 1989 and Priestle et al., supra also submitted their coordinates simultaneously and a comparison of the present structure (FIG. 2) with these two revealed that all the three are almost identical with a few deviations in the surface loops. The deviations observed in the final model for bond lengths, bond angles and for planar deviations are found to be well within the ideal targeted variances.

Atomic isotropic mean-square displacement parameters (B) were refined for all non-hydrogen atoms including solvent oxygen atoms. The mean B value for all the 1219 protein atoms is 38.1 Å$^2$ and that of 115 solvent atoms is 67.3 Å$^2$, resulting in a mean B value of 40.7 Å$^2$ for all the 1334 atoms included in the refinement. As expected, the main chain atoms have a lower mean B value than side chain atoms. The regions of the molecule showing the highest B values are mainly in loops connecting β strands (residues 33.35, 49–54, 106–108 and 137–141) and residues in the amino and carboxy termini regions. The same characteristics of very high thermal fluctuations in the same segments of this molecule has been observed in the other two structures also.

Of the 115 solvent molecules identified, there are nine internal water molecules held tightly within the cavities of the protein and 51 waters in the first solvation shell of the protein, interacting directly with the protein's main chain or side chains. The remaining waters are either in the second shell or in between the symmetry related molecules in the crystal lattice. Crystal packing analysis shows that long uninterrupted solvent channels run parallel to the crystallographic a and b axes. As expected almost all the charged residues show a much larger accessibility than the mean, while hydrophobic residues Val, Leu, Ile and Phe are less accessible than the mean. Glycines and prolines display a high mean accessibility. All the tyrosines are exposed and make hydrogen bonding contacts with solvent molecules.

EXAMPLE 3

Site Directed Mutagenesis of IL-1β

An IL-1β expression plasmid for site-directed mutagenesis is constructed as described in Kamogashira et al., *Biochem. Biophys. Res. Comm.* 150, 1106 (1988). This expression plasmid contains the coding region of IL-1β under the control of trp promoter. The plasmid also contains the intergenic region of the phage f1 as used for isolation of single stranded DNA for site-directed mutagenesis and for expression of IL-1β protein.

The site directed mutagenesis of Glu25 to Ala is then conducted in accordance with the techniques of Zollen et al., *Methods in Enzymology*, Academic Press, Wu, Grossman and Moldane eds., Vol. 100, pp. 468–500 (1983). Appropriately mutated oligonucleotides are phosphorylated, and then mixed with appropriate amounts of single stranded DNA template from the expression vector, DTT, dNTPs, ATP, hybridization buffer, T4 DNA ligase and Klenow DNA polymerase I as described in Zollen et al. and Kamogashira et al. Samples from the ligation mixture are then used to transform competent *E. coli* MV 1304 cells.

Colonies containing mutated plasmids are identified by hybridization with $5'$-$^{32}P$-labeled oligonucleotides. Plasmid DNA is subjected to nucleotide sequence analysis to confirm the presence of the desired mutation by the methods of Sanger et al., *Proc. Natl. Acad. Sci. USA* 74, 5463 (1977).

The mutant IL-1β protein is prepared by induction of the trP promoter after tryptophan starvation of the *E. coli* with mutant plasmid. Growth of *E. coli* is in a suitable medium such as M9 medium containing 0.4% glucose and 1.0% casamino acid. Mutant protein is recovered by standard techniques set forth in Laemmli, *Nature* 227, 680 (1970) and Kahn et al., *Methods in Enzymology*, Academic Press, Wu, Grossman and Moldane eds, Vol. 68, pp. 268–280 (1979).

Other mutant forms of IL-1β form any of the other disclosed mutations may be produced using appropriately mutated oligonucleotides in the above procedure. As discussed in the specification, some of these mutant forms of IL-1β will have IL-1β antagonist activity and some will have IL-1β agonist activity.

EXAMPLE 4

Binding Analysis of IL-1β Mutant

An IL-1 receptor binding analysis of the IL-1β mutant of Example 3 is performed using the published procedure of Dower et al., *Nature* 324, 341 (1986). This procedure utilizes the IL-1 receptors on human dermal fibroblast cells. Briefly, 10 μl of the mutant IL-1β of Example 3 in 10 μl of phosphate (0.015M) buffered saline (0.15M) pH 7.2 is added to 10 μl of sodium borate (0.1M) buffered saline (0.15M) pH 8.5. The mutant IL-1β is then reacted with 1 mCi of Bolton Hunter reagent according to the manufacturer's instructions for 12 hours at 8° C. Then, 30 μl of 2% gelatin and 5 μl of 1M glycine ethyl ether is added, and the mutant IL-1β separated from the unreacted reagent on a 1 μl bed volume Biogel P6 (Biorad) column. Approximately 50–60% incorporation of the radiolabel is observed. Precipitation of the $^{125}I$-IL-1β mutant in 1% 2% gelatin carrier using 10% trichloroacetic acid on gel filtration column shows that >98% of the $^{125}I$ label is protein bound after P6 purification.

Human dermal fibroblasts are obtained from the American Type Tissue Culture Collection (CRL 1229, passage 5) and propagated in monolayer cultures in DMEM 10% fetal calf serum. The fibroblasts are harvested for the binding assay by treatment with PBS containing EDTA (0.5 mM) to avoid proteolysis of the receptor.

The fibrobalst cells are then incubated with $^{125}I$-labelled mutant IL-β and unlabelled IL-1β in 150 μl of RPMI 1640 with 1% BSA, 0.1% sodium azide and 20 Mm HEPES pH 7.4 for 2 hours at 8° C. on a rocker platform in round bottom well microtire plates. Cells and bound radiolabelled mutant IL-1β are then separated from unbound label by centrifuging 60 μl aliquots of the reaction mixtures through 200 μl of phthalate oils in 400 μl polyethylene centrifuge tubes and excising the tips with a razor blade as taught by Segal et al., *J. Immun.* 118, 1338 (1977).

Equilibrium binding data are analyzed using a bimolecular binding model as described by Dower et al., *J. Exp. Med.* 162, 501 (1985). The values for nonspecific binding are determined by fitting a straight line passing through the origin to data obtained from binding of the $^{125}I$-labelled mutant IL-1β to human fibroblast cells in the presence of a 100-fold molar excess of unlabelled IL-1β. The mutant IL-1β from Example 3 is found to have almost a 100% binding profile to the human fibroblast cells. However, other IL-1β mutants wherein the Lys103 has been mutated will have a significantly lower binding profile due to the mutation at the receptor binding surface.

EXAMPLE 5

Bioassay of IL-1β Mutant

The level of IL-1β activity of a composition is commonly determined by its ability to inhibit the growth of human melanoma cells A375.S1. This property of IL-1β is referred to as its growth inhibitory factor (GIF) activity. One GIF unit is defined a the receiprocal of the sample dilution necessary to yield about a 50% cytostasis or cytolysis in 4 day old cultures of the melanoma cells.

The IL-1β mutant of Example 3 is used in this assay as described in Lackman et al., *J. Immunol.* 136, 3098 (1986), and exhibits a decrease in GIF activity as compared to the GIF activity of IL-1β. Other antagonist mutants of IL-1β are expected to exhibit similar decreased GIF activity, whereas agonist mutants of IL-1β are expected to exhibit GIF activity at a similar level to that of IL-1β.

While the invention has been described in connection with specific embodiments thereof, it is understood that the invention is capable of further modifications. This disclosure is intended in an illustrative rather than in a limiting sense, as it is contemplated that modifications will readily occur to those skilled in the art, within the

What is claimed is:

1. A modified interleukin-1β polypeptide antagonist which inhibits the biological activity of interleukin-1β, said polypeptide having the same amino acid sequence as IL-1β but having an aliphatic chain amino acid at the 25 position of the amino acid sequence.

2. The modified interleukin-1β polypeptide antagonist of claim 1, wherein the aliphatic chain amino acids are selected from the group consisting of alanine, valine, leucine, isoleucine and glycine.

3. The modified interleukin-1β polypeptide antagonist of claim 2, wherein the aliphatic chain amino acid is alanine.

* * * * *

UNITED STATES PATENT AND TRADEMARK OFFICE
CERTIFICATE OF CORRECTION

PATENT NO. : 5,349,051
DATED : September 20, 1994
INVENTOR(S) : Balasubramanian VEERAPANDIAN It is certified that error appears in the above-indentified patent and that said Letters Patent is hereby corrected as shown below:

On the title page, Item [54] and Column 1, Line 2, the title should read as follows:

--MODIFIED INTERLEUKIN-1β--

Signed and Sealed this

Sixth Day of December, 1994

Attest:

BRUCE LEHMAN

Attesting Officer            Commissioner of Patents and Trademarks

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
      ( A ) LENGTH: 5 amino acids
      ( B ) TYPE: amino acid
      ( D ) TOPOLOGY: linear ( i i ) MOLECULE TYPE: peptide ( v ) FRAGMENT TYPE: internal ( v i ) ORIGINAL SOURCE:
      ( A ) ORGANISM: Homo sapiens ( x i ) SEQUENCE DESCRIPTION: SEQ ID NO:1:

Glu  Cys  Met  Met  Lys
   1                    5